United States Patent [19]

Haase

[11] 4,201,222
[45] May 6, 1980

[54] METHOD AND APPARATUS FOR IN VIVO MEASUREMENT OF BLOOD GAS PARTIAL PRESSURES, BLOOD PRESSURE AND BLOOD PULSE

[76] Inventor: Thomas Haase, 2996 Alta Laguna, Laguna Beach, Calif. 92651

[21] Appl. No.: 829,420

[22] Filed: Aug. 31, 1977

[51] Int. Cl.² .......................... A61B 5/02; A61B 5/00
[52] U.S. Cl. .................................. 128/634; 128/666; 128/667; 128/673; 128/689
[58] Field of Search ................. 128/2 L, 2.05 D, 2 E, 128/2.07, 2.05 P; 73/19, 23, 23.1; 356/39, 40, 41, 42; 23/254 R, 254 E

[56] References Cited
U.S. PATENT DOCUMENTS

| 3,123,066 | 3/1964 | Brumley | 128/2 L |
| 3,412,729 | 11/1968 | Smith | 128/2.05 R |
| 3,822,695 | 7/1974 | Takayama | 128/2 L |
| 4,003,707 | 1/1977 | Lübbers et al. | 23/232 R |
| 4,041,932 | 8/1977 | Fostick | 128/2 G |

OTHER PUBLICATIONS

Webster's Seventh New Collegiate Dictionary, p. 528, (1961).

Primary Examiner—Robert W. Michell
Assistant Examiner—Jeffrey W. Tayon
Attorney, Agent, or Firm—Gordon L. Peterson

[57] ABSTRACT

An optical catheter including an absorption chamber and distensible semipermeable diaphragm are disclosed for the simultaneous measurement of blood gases, blood pressure and pulse rate.

7 Claims, 6 Drawing Figures

FIG. 3.
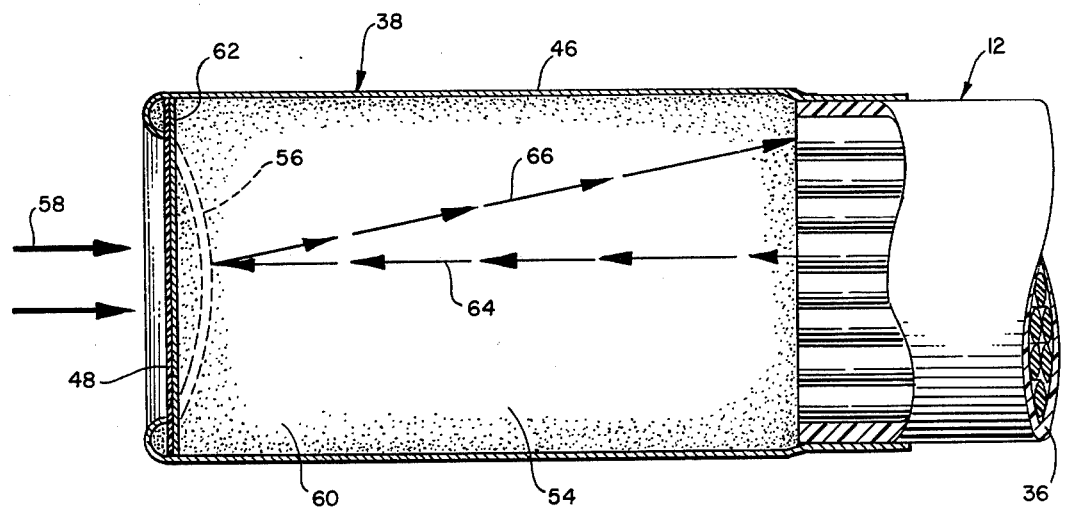
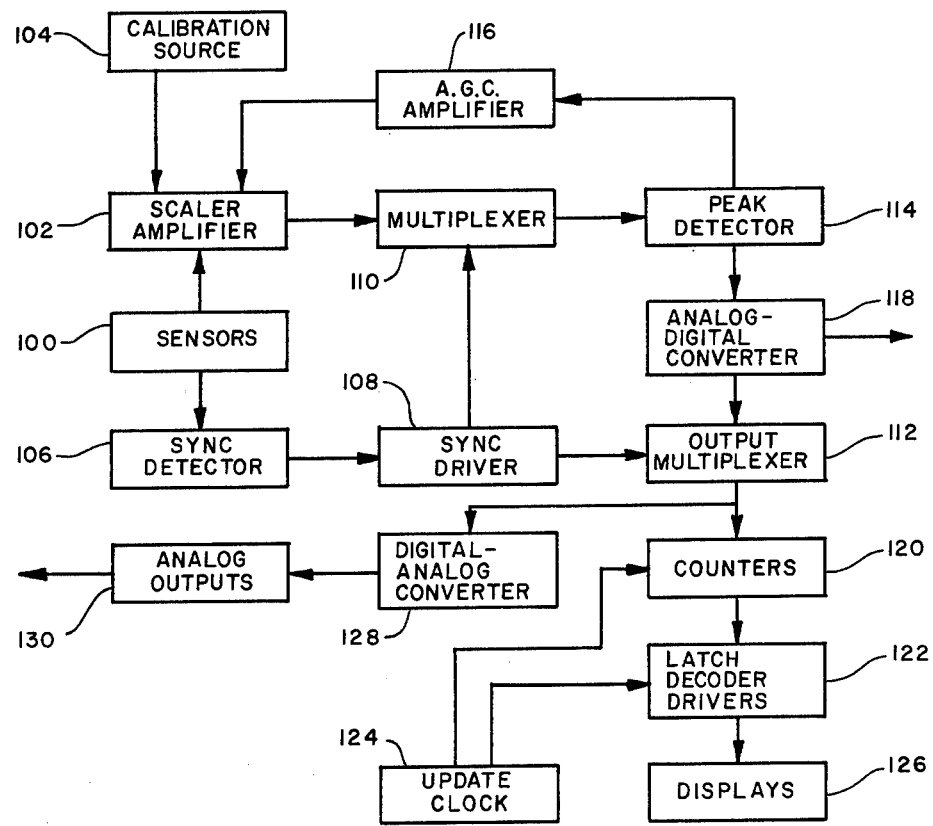
FIG. 4.

METHOD AND APPARATUS FOR IN VIVO MEASUREMENT OF BLOOD GAS PARTIAL PRESSURES, BLOOD PRESSURE AND BLOOD PULSE

BACKGROUND OF THE INVENTION

This invention relates to cardiovascular monitoring and, more particularly, to an absorption spectroscopic catheter for the in vivo measurement of blood gas partial pressures as well as blood pressure and pulse rate.

Pressure transducer catheters are well-known (References 1, 2), as are electrolytic type catheters for determining blood gases (3). Various optical catheters have been conceived for the measurement of gas content in blood (4–9) and for providing both blood gases and pressure-pulse rate data (8). Some of such systems utilize fiber optic technology to introduce light in the red-visible region of the spectrum into the bloodstream which is reflected by blood molecules. The reflected light is then colorimetrically analyzed to determine blood color from which information pertaining to oxygen saturation can be derived. This information, however, is actually a ratio of the number of oxygenated hemoglobin molecules to non-oxygenated hemoglobin molecules, and does not provide data in terms of the partial pressure of oxygen which is a vital parameter vis-a-vis the life of the catheterized patient. Another disadvantage of colorimetric systems is that carbon dioxide content in the blood is not directly obtainable.

Other catheter systems utilizing the arts of gas chromotography (10) or mass spectrometry (11) have been devised to measure cardio-vascular functions. Such systems, however, generally require the removal of a blood sample from the body before analysis can take place. The analytical components are very large and are usually located in laboratories which are often far removed from the operating room. Once the blood reaches the laboratory the analysis response time of such systems is typically slow. Delay is a primary disadvantage of mass spectrometric and gas chromotographic systems. Expense is a further disadvantage.

The principles of absorption spectrometry are well-known and find application in a number of analytical systems, procedures and devices. These principles, however, have not been applied to the rapid and accurate in vivo analysis of dissolved gases in blood. Briefly, and in a very much simplified manner, the principle of operation of the present absorption spectrometry catheter system is described as follows.

Each atom or molecule absorbs and radiates electro-magnetic radiation in discrete quantitative increments at a number of discrete levels of energy. In the present instance, the electro-magnetic energy is in the energy range referred to as "light," including both the visible and the invisible infrared and ultra-violet regions of the light spectrum. When a light beam of a specific energy level, i.e. wavelength, preferably of only one wavelength, i.e. monochromatic light, is passed through a chamber containing a specific substance which absorbs at that wavelength, the amount of absorbed light, and hence the reduction in the intensity of the light beam, is proportional to the number of atoms or molecules of the substance in the chamber which interact with the incident radiation. The ratio of intensity incident light, $I_o$, to the intensity of the exit light, $I_f$, is a measure of the absorbed light and, therefore, a measure of the amount of the substance in the absorption chamber.

Actually, any given substance will absorb light of many differnt energy levels (wavelengths), some wavelengths being strongly absorbed and others much less strongly absorbed. This variation in amount of absorption with wavelength is referred to as the absorption spectrum of the particular material.

When the substance to be measured is a gas, such as oxygen or carbon dioxide, it is convenient to measure the amount of the gas present in a chamber of defined dimensions. According to the gas law, the pressure of the gas in such a chamber is directly proportional to the amount, or number of molecules, of gas in the chamber. Thus, it is possible to measure directly the pressure of a given gas in the chamber simply by measuring the total amount of the gas in the chamber. Where more than one gas is present the pressure contribution of each constituent gas is referred to as the "partial pressure" of that gas.

In any system which includes gases, whether it be a gaseous system, such as a chamber of defined proportions, or a liquid system, such as flowing blood, each gaseous component exerts a pressure proportional to the total amount of the gas in the system. Thus, each gas dissolved in the blood exerts a "partial pressure" in the blood stream. If such a system having a partial pressure of a given gas, for example blood with an oxygen or carbon dioxide partial pressure, is placed in contact with a barrier which is permeable to the gas but not to the blood, the gas will permeate and diffuse through the barrier, i.e. dissolve in one side and out the other, until the partial pressure of that gas on the other side of the barrier equals the partial pressure of the gas in the blood stream. Actually, the pressures on each side of the barrier need not be exactly equal since there are permeation factors, and other factors, which effect the flow through the barrier; however, the gas will flow through the barrier until an equilibrium value is reached at which time the rate of diffusion through the barrier is equal in both directions.

This principle is applied in the present invention by placing a catheter which includes a chamber of defined dimensions in the blood stream. All or part of the wall of the chamber is made of a barrier membrane which is permeable to oxygen and carbon dioxide and/or selected other gases, referred to as a semipermeable membrane. The partial pressure of a given gas in the chamber, at equilibrium, is directly proportional to the partial pressure of gas in the blood. Accordingly, by measuring the partial pressure of the gas in the chamber, by measuring the total amount present as discussed before, the partial pressure of dissolved gas in the blood can be determined. The unique application of these principles in the apparatus and systems and methods of this invention are an important feature of this invention.

Absorption spectroscopy is particularly useful where emission spectra are difficult to obtain due to the high energy levels required to achieve electronic configurations excitations. This is especially true of polyatomic and diotonic gases. For example, absorption spectroscopy has been successfully employed to measure the ozone level of the atmosphere. Since low energy radiation is sufficient for obtaining absorption spectra, measuring systems based on this concept are very advantageous and well suited for use in the in vivo measurement of cardiovascular functions. The development of high infrared transmissive optical fibers has made possible the efficient utilization of the absorption concept in blood catheters. The use of absorption chambers in conjunction with such catheters provides for flexible and accurate monitoring of one or a combination of several blood gases.

The preferred embodiment of the present invention allows for the simultaneous measurement of oxygen and carbon dioxide partial pressures, vital indicators with respect to cardiovascular performance. Furthermore, the same monitor is easily adapted to also measure the equally vital overall blood pressure and pulse rate, thereby embodying a complete, yet convenient and accurate, monitoring device. Convenience in use and mobility of the monitor, because of its small dimensions and reduced space requirements of the optical and electronic components, are important features of the present invention. Use of monochromatic light of strongly absorbed wavelength provides both accuracy and sensitivity for both gases, with minimum effect from the presence of other gases. Response time of the absorption catheter is very short, only about three seconds.

SUMMARY OF THE INVENTION

The present invention provides an optical catheter system, based on the art of absorption spectroscopy, for the accurate and efficient cardiovascular monitorization of blood gas content, as well as overall blood pressure and pulse rate.

In general, the catheter of this invention comprises a pair of elongate fiber optic bundles, which may be randomly mixed with each other, in an elongate sheath of any of several biologically compatible materials. The fiber optic bundles are adapted at the proximal end to receive incident monochromatic radiation, $I_o$, of known intensity and predetermined wavelength and to transmit the incident radiation the lengths of the catheter to an absorption chamber at the distal end of the catheter. The absorption chamber may be of any configuration but is conveniently of generally cylindrical shape with the fiber optic bundles at one end directing the incident radiation the length of the chamber to a reflective surfaced semipermeable membrane forming the other end of the chamber. In this configuration the radiation is absorbed by gases present in the chamber during two passes through the chamber, to the mirror and from the mirror back to the fiber optic bundle. The remaining, or exit radiation, is transmitted by the fiber optics back along the length of the catheter to radiation detectors which measure the intensity of the final radiation, $I_f$. It is the ratio $I_o/I_f$ which is proportional to the partial pressure of the dissolved gas in the blood stream. In the preferred form, the distal wall of the chamber serves both as a semipermeable membrance and as a mirror, being coated with gold or some other reflective coating to about a 50% reflectivity; however, separate semipermeable membranes, e.g. in the cylinder walls, could be provided to result in the same basic chamber. Similarly, the chamber may be spherical or of some other configuration. It is intended that the specific embodiments referred to here and hereinafter are not limiting but are merely exemplary.

In accordance with the preferred embodiment of this invention, the blood partial pressures of two gases, oxygen and carbon dioxide, are concurrently measured and displayed. Where two gases are present in the chamber, each will absorb light passed through it, to one degree or another, depending upon the wavelength of the incident light rays. Thus, the absorption by both gases will contribute to the decrease in intensity of the incident light, that is, $I_o$ less $I_f$, thereby making inaccurate the measurement of either one of the two gases. It is therefore necessary for the measurement of a first gas, to supply light to the chamber of a wavelength at which absorption by that particular gas is very high, and at which absorption by the other gas present is very low. Similarly, absorption analysis of the second gas should utilize light of a wavelength at which absorption by that gas is high and at which absorption by the first gas is very low, or negligible.

The present invention accomplishes this objective by utilizing light with a predeterined wavelength of approximately 7596 angstroms for the absorption analysis of oxygen, and of approximately 2 microns for the measurement of carbon dioxide. At these wavelengths, the respective absorption by carbon dioxide and oxygen, as well as other gases present, water vapor and nitrogen will be negligible. The optical fibers employed by the present invention are unique in that they exhibit high transmissive qualities, that is, above 30%, of light in the infrared region.

Two distinct light sources, one visible and one infrared, are provided for the production of light beams of these wavelengths. The visible source in the preferred embodiment is a laser, well-known for the coherent and monochromatic nature of its light rays (22-24). Dual detectors, responsive to light in the visible and infrared regions of the spectrum, respectively, are also provided.

Light from the two sources is alternately pulsed by the use of an optical multiplexer, referred to as a "chopper," towards the incidence channel of the fiberoptical system for transmission to the chamber. Pulsing is necessary not only because there are two light sources and only a single incidence channel, but also because a continous beam of light falling on the detectors substantially dampens its sensitivity and reduces the signal to noise ratio. The chopper herein employed, however, is novel in that it not only produces the necessary pulsation of light, but also simultaneously synchronizes the alternate pulsation of light from two light sources, and the alternate detection of reflected light rays by two detectors.

A further advantage of the present invention is that it provides for the measurement of gases present in the blood stream, other than oxygen and carbon dioxide. The structure and concept of this invention allows the absorption analysis of one or a combination of several gases.

Finally, besides the measurement of blood gas partial pressures, the present invention is capable of simultaneous monitoring of overall blood pressure and pulse rate. The semipermeable window contained in the absorption chamber is made of a flexible substance which allows it to deflect in response to blood pressure and pulse rate. These responsive deflections are transmitted to the light by the window at the point of reflection, and are exhibited by the reflected light in the form of amplitude modulations. These modulations are sensed by the detectors which generate electronic signals in response thereto. These signals can then be properly converted and visually displayed to provide the instantaneous and complete monitorization of cardiovascular functions, including blood gas partial pressures, overall blood pressure and pulse rate.

These and other advantages of the present invention are readily apparent by reference to the drawings in which:

FIG. 3 is a section view, taken along lines 3—3, of the sensor end tip showing absorption chamber and peripheral sensor construction;

FIG. 4 is a block diagram illustrating the electronic analog to digital conversion of the output signals.

DETAILED DESCRIPTION OF THE PREFERRED EMBODIMENT

Figure 1:
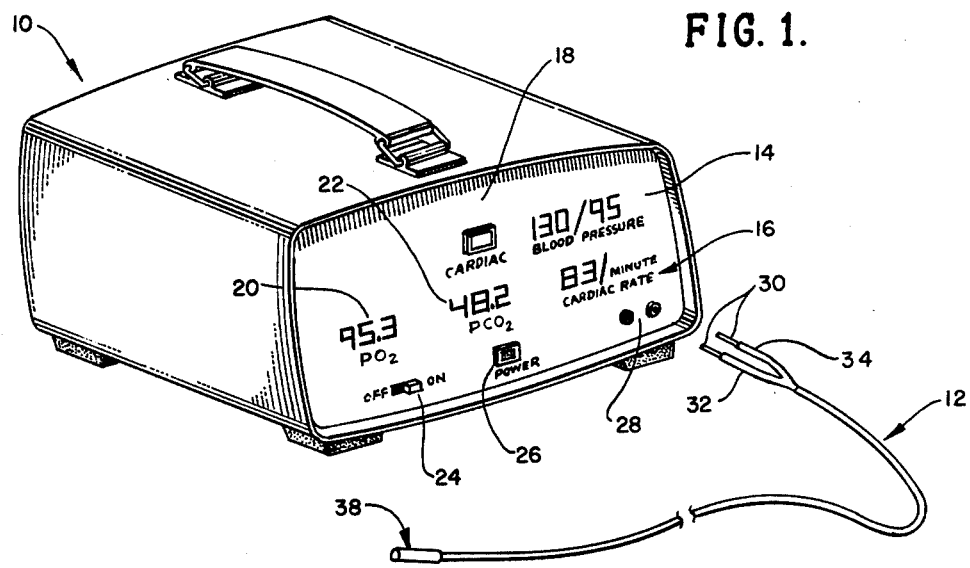
FIG. 1 is a perspective drawing of the Cardiovascular Monitor including digital display of oxygen and carbon dioxide partial pressures, blood pressure and cardiacrate, detectable optical catheter chambered sensor end tip.

Shown in FIG. 1 is an exemplary cardiovascular moniter with catheter attachment, indicated generally at 10 and 12, respectively, which embody the present invention. Other forms of equipment of like function, e.g. using a strip chart display are obviously within the scope of this invention. Moniter 10 provided for the visual digital display of blood pressure 14, both systolic and diastolic, cardiac rate 16, pulse rate indicator light 18, and partial blood pressures of oxygen and carbon dioxide, 20 and 22, respectively. On/off switch 24 and power light indicator 26 are also shown.

Housed within monitor 10 is the optical multiplexing system of the present invention, including light sources, detectors and rotary multiplexor, as well as the electronic analog-to-digital conversion system, necessary for the processing and display of the cardiovascular data. This mode of housing and display is, however, merely a preferred example. In many cases it may be desirable to record, by means of a strip chart for example, the signals corresponding to the above data.

The monitor face is provided with input/output connection 28, which receives dual jacks 30 of the bifurcated optical catheter 12. Incidence channel 32 and reflection channel 34 combine to form catheter body 36, the former for transmitting light to sensor end tip 38 and the latter for return transmission of reflected light. The construction of the bifurcated fiber optical system will be dealt with in more detail below.

Figure 2:
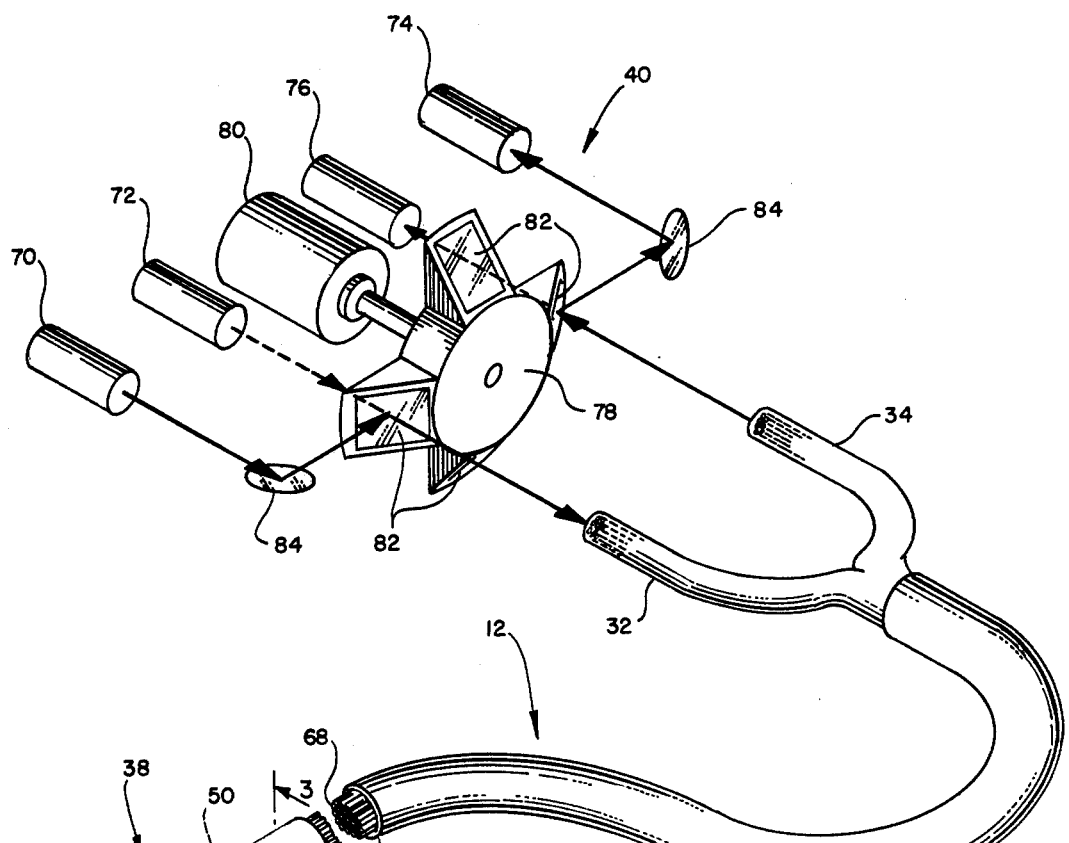
FIG. 2 is a perspective and schematic diagram optical multiplexing system and fiber optics of the preferred embodiment of the present invention.
Figure 2:
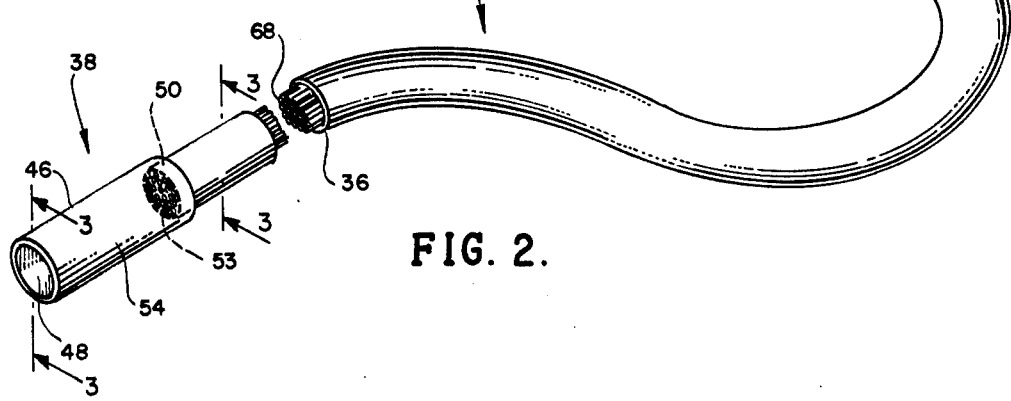

FIG. 2 illustrates the primary components of the preferred embodiment, the optical multiplexing system 40, fiber optical catheter 12, and the sensor end tip 38 and the manner in which these systems interface. Sensor 38 is generally defined as a cylindrical housing 46, fitted at one end with a semipermeable window 48. The sensor housing can be constructed of stainless steel, or of less rigid materials such as nylon, ABS or of any of the well-known biologically acceptable materials. Its diameter is approximately 2 mm and measures about 4 mm in overall length.

The window material must be flexible, so as to be sensitive to blood pressure and cardiac rate, and also permeable, in the preferred embodiment, to oxygen and carbon dioxide. Sylastic brand (General Electric) silicon rubber of thickness about 10 microns is generally accepted as a biologically compatible semipermeable membrane material and is quite satisfactory.

A circular light aperture 50 generally defines the proximal end of housing 46 and receives the non-bifurcated end of fiber optic bundle 53, thereby allowing the entrance and exit of light into and out of sensor end tip 38.

The detailed construction of the sensor end tip 38 is shown in FIG. 3. Sensor housing 46 narrows at its proximal end to facilitate attachment to the optical catheter body 36. Window 48 is affixed to the housing using an autoclavable epoxy glue. The deflection of the window 48, shown in phantom line 56, is due to the pressure of the blood on its exterior surface, indicated by the arrows 58, the frequency of such deflections being dependent upon the rate of heartbeat. In addition to flexing in response to blood pressure and pulse rate, the window is permeable to oxygen and carbon dioxide molecules dissolved in the blood.

Gas molecules 60 diffuse through the window membrane into the absorption chamber 54 until equilibrium is reached. At this point, the partial pressures of $O_2+CO_2$ inside chamber 54 will equal, or at least be directly proportional, to the surrounding partial pressure of these gases in the bloodstream. A reflective coating 62 is applied to the interior surface of the window using conventional vacuum deposit or evaporational techniques. The coating material can be gold or aluminum and is applied so as to exhibit an optical density of about 46%, not opaque enough to reduce to any substantial degree the permeability of the window and yet sufficient to allow for reflection of incident light rays, as shown by arrows 64 and 66.

Body 36 of optical catheter 12 is comprised of a sheathing material such as flexible polyvinyl chloride, nylon, Tygon, chlorinated rubber, or other biocompatible material. The body is, conveniently, shrink molded for attachment to housing 46 of sensor end tip 38.

Referring again to FIG. 2 the bifurcated construction of the fiber optical catheter 12 is shown. Ten fibers, in a typical structure, each constitute the incidence and reflection channels 32, 34 of the catheter, to form the 20-fiber, randomly mixed bifurcated bundle, shown in section at 68. Corning fiber optics No. 44-49016-1499 is a presently preferred fiber optic material.

The optical multiplexing system, indicated generally at 40, consists essentially of red visible and infrared light sources 70 and 72, visible and IR detectors 74 and 76, and an optical multiplexer 78, referred to as a "chopper." The rotary chopper 78 is powered by motor 80. Visible source 70 is a laser which produces light with an approximate wavelength of 7596 angstroms and intensity of 5-10 mw, e.g. Spectraphysics Model 142 or Model 335 used for the absorption analysis of oxygen. A laser source is preferred because of the characteristically coherent and monochromatic narrow beam produced thereby. A further advantage is the reduced size of the source optics required, providing for a monitor of reduced dimensions.

The infrared source 72 is a standard incandescent reflective source for the absorption measurement of carbon dioxide. For the reasons discussed above, a carbon dioxide laser is a desirable source but cost considerations presently suggest the use of conventional IR source. The wavelength of light produced by the IR source is approximately 2 microns and has an intensity of 250-300 watts.

The visible detector 74 consists of a silicon phototransistor, peaked for detection via narrow band filters of light wavelengths of around 7596 angstroms. Texas Instruments Co. Model TIL 78 is an example of such a detector. While a silicon phototransistor could be utilized as the IR detector 76, a triglycine sulfate crystal detector is preferred because of its proper gain special frequency and time response. The IR detector is selected and adjusted to sense light wave lengths of around 2 microns. Narrow band filters of, respectively, 7596 angstroms and 2 microns with a band width of ½A are part of the detector and not depicted separately.

It is well-known that a continuous beam of light falling upon an optical detector will substantially dampen its response, and that pulsation of the incident light is therefore necessary. Optical chopper 78 accomplishes this result, as well as the multiplexing of two discrete light rays down a single fiber optical channel. As shown in FIG. 2, each 90° rotation of the chopper wheel 78 allows light procuded by the visible source 70 to be reflected by one of its four prisms 82 towards the incidence channel 32 of fiber optic catheter 12. Instantaneously, the incident light ray will be reflected by window 48 for return transmission via reflection channel 34, whereupon it impinges upon another prism located on the chopper 180° from the first. Turning of the visible beam at the locations shown in FIG. 2 is provided for by totally reflective optical flats 84.

With each 45° rotation of the chopper, the infra-red light produced by IR source 72 is allowed to pass through and enter the incidence channel 32 for transmission to the absorption chamber 54. Reflected IR light will similarly pass through the chopper for direct sensing by IR detector 76.

The electrical output signals produced by the sensors, indicated generally at 100, in response to reflected light rays are processed in accordance with the analog/digital conversion electronics system shown in FIG. 4. The analog signal first undergoes pre-calibration in a conventional scaler amplifier 102 where it is scaled to correspond to the voltage input limits of the microprocessor.

A calibration source 104, which may be any of a large number of stable signal generators of conventional design, is selectively fed to the scaler amplifier 102 to ensure electronic stability. The sensor output also triggers the syncronization detector 106 which, along with syncronization driver 108, generates a sync pulse to ensure proper syncronization in the input multiplexer 110 and the output multiplexer 112. The processed signal from the multiplexer 110 is processed by a peak detector 114 which senses the maximum amplitude of each peak of the alternating signal resulting from the optical multiplexer. An automatic gain control amplifier 116 receives an output signal from the peak detector and feeds the scaler amplifier 102 to ensure proper voltage input to the multiplexer 110. The peak detector output is an analog signal which is converted to a digital signal for further processing by a conventional analog to digital converter 118 which feeds the digital signal to the output multiplexer 112 where the signal is processed for individual display and may then be displayed as a digital signal by means of counters 120, catch decoder drivers 122 over predetermined time intervals controlled by the update clock 124 and then visually presented by displays 126 which may be conventional neon glow tube devices of any design, or any other digital signal responsive display device. A plotter or printer could, for example, be used in lieu of the neon glow tubes of the exemplary embodiment depicted in FIG. 1. In addition, or alternatively, the processed signal may be converted by a conventional digital to analog converter 128 to be displayed by an analog display device 130, such as a conventional strip chart recorder.

No novelty or unique features reside in the electronic circuits; indeed, all electronic circuits and signal handling devices and displays are well-known and generally used thoughout the electronics and instrument industries and are described in numerous standard texts and other publications. See, for example, Brophy, J. J., 1972, *Basic Electronics for Scientists*, 2nd Ed., McGraw-Hill, New York; Offner, F. F., 1967, *Electronics for Biologists*, McGraw-Hill, New York; Vassos, B. H. and Ewing, G. W., *Analog and Digital Electronics for Scientists*, 1972, Wiley-Interscience, New York. Off-the-shelf electronic signal processing instruments which are adaptable for producing suitable readout of the signals are available from a number of instrument manufacturers.

In use, the optical catheter 12 is inserted into the bloodstream such that sensor end tip 38 is in the desired location. Carbon dioxide and oxygen molecules dissolved in the blood diffuse across the permeable window 48 and occupy absorption chamber 54. The systolic and diastolic pressures of the blood produce corresponding deflections in window 48 which occur at the frequency of the pulse rate. The rotary action of the chopper 78 multiplexes alternate light rays of known intensities down incidence channel 32 of the optical catheter 12 to chamber 54. As shown in FIG. 3, incident light rays 64 pass through the chamber, and are reflected by the reflective coating 62 of window 48 back through the chamber, whereupon the reflected rays 66 enter one of the fibers constituting reflection channel 34 for transmission to the detectors. The reflected light pulse is amplitude modulated at the point of reflection by the deflections of window 48, resulting from pulsing of the blood and the average blood pressure. Calibration of each catheter, or selection of like-sensitivity catheters, is required for quantitization of the signal output; however, it will be apparent from the geometry of the sensor chamber that an increase in blood pressure, either long term or transitional, will cause distension of the membrane and will result in greater scattering of the light thus reducing the proportion of the light reflected to the reflecting channel optical fiber bundle. This phenomenon, in itself, is known (8) and therefore, no detailed discussion is required.

The light of each frequency, in addition, undergoes two absorptions by the respective gas to which each corresponds. For example, light from the visible source 70, having a predetermined wavelength of about 7596 A, precedes the pulse of light from the IR source 72 down the incidence channel to the chamber. As this pulse of light twice traverses the chamber, its energy is absorbed by the oxygen molecules present. $CO_2$ and other gases, on the other hand, will absorb only a negligible amount of energy. Therefore, the intensity of the reflected visible beam, as determined by the visible detector 74, when compared to the known intensity of the incident beam, will correspond accurately to the partial pressure of oxygen in the absorption chamber and bloodstream. Partial pressure of gases is displayed or recorded in units of mmHg.

The output signals of the detectors will contain information relating not only to the intensities of reflected light, but also to blood pressure and pulse rate. These data then enter the electronic processing system, illustrated in FIG. 4, previously described.

Figure 5:
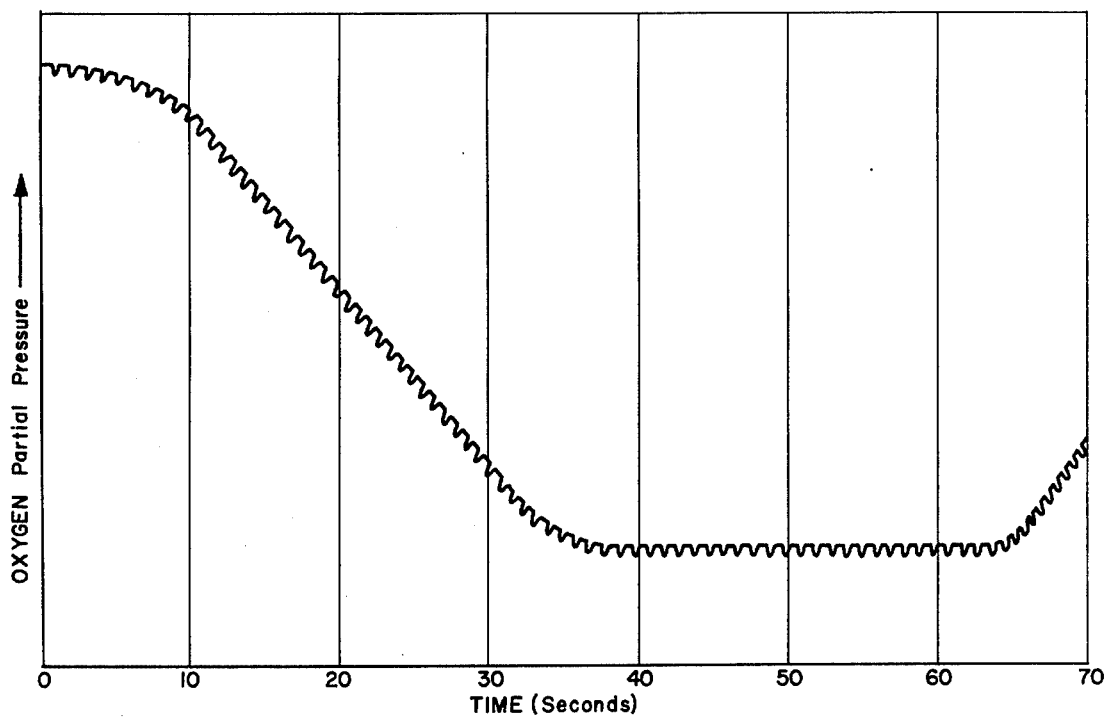
FIGS. 5 and 6 are signal output waveforms.

FIG. 5 depicts, in a very general fashion, the gross signal that may be obtained from an oxygen sensor of the type described, the ordinate indicating increasing dissolved oxygen, partial pressure, in the blood, increasing upwardly, the abscissa indicating time, from an arbitrary zero starting point, in seconds, increasing to the right. As the partial pressure of oxygen in the blood increases (in the course of graph of FIG. 5 the increase being very rapid simply to illustrate the type of signal output) the absorption by the oxygen in the sensor chamber increases, thus decreasing the intensity of the output signal. This gross decrease in signal is depicted by the sharp downward turn of the output signal curve, followed by a levelling as the oxygen partial pressure stabilizes and then by a sharp decrease accompanied by a rapid, shallow pulse at the right of the figure. The pulse rate and pressure is carried on the signal in the form of a more rapid amplitude modulation component which is effectively averaged electronically when considering the oxygen partial pressure signal. The relative magnitude of the pulse and partial pressure signals depends upon the geometry of the sensor and may be predetermined at any desired ratio by making the chamber longer and the membrane smaller to increase the partial pressure to pulse signal ratio or by making the membrane larger and the chamber smaller to increase the pulse to partial pressure signal ratio.

Figure 6:
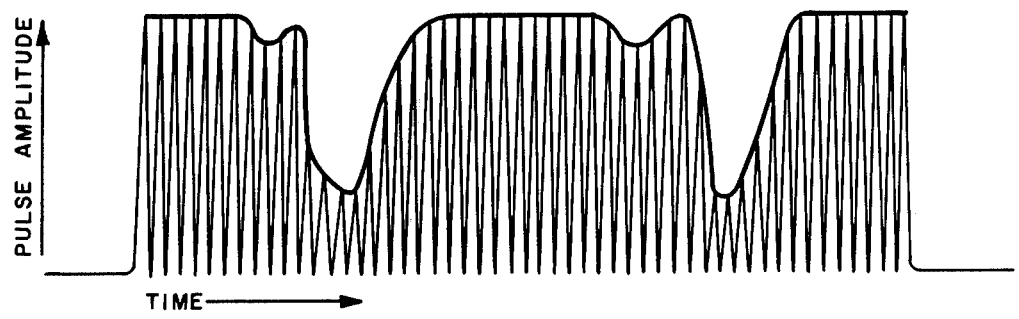

FIG. 6 is short time period depiction of a signal of the type depicted in FIG. 5 except that the pulse to partial pressure ratio is very much higher than that ratio in FIG. 5, simply to illustrate the manner in which the pulse rate-blood pressure data are carried by the signal. In FIG. 6, the partial pressure component is ignored because of the short time duration, the entire figure representing only about two seconds, and to focus upon the pulse rate-blood pressure data. The signal is in the form of a modulated AC, the AC component resulting from the optical multiplexer, the amplitude modulation resulting from the distension of the membrane by the pulsation pressure in the blood vessel in which the catheter dwells during use. In practice, the pulse rate is read directly, e.g. 83 pulses per minute, and the pressure is converted electronically to correspond to the blood pressure as determined by the conventional sphygmometer, e.g. 130/95, the conversion factor being determined empirically.

As pointed out before, the invention resides in the application of absorption spectrometry to the in vivo determination of oxygen and carbon dioxide, or other gases, in blood and, more particularly in the design and operation of the catheter and optical system and not in the manner or means for electronically processing and displaying the output signal. Considerable variation in the precise manner and apparatus in which the invention is embodied is contemplated without departing from the concept of the invention of the scope of the invention as defined in the claims, it being immaterial to the invention that any particular method or means of electronic signal processing and display is used. It is, accordingly, the intent that the claims which follow be read in light of and consistently with the scope and nature of the inventive concept and the manner in which that concept is utilized and not upon the merely exemplary embodiment by which the invention is depicted and described hereinbefore.

REFERENCES CITED IN THE SPECIFICATION

The following references, and those specifically referred to in the specification, are incorporated herein as if fully set forth.
1. U.S. Pat. No. 3,249,105, Polanyi, May 3, 1966.
2. U.S. Pat. No. 3,273,447, Frank, Sept. 20, 1966.
3. U.S. Pat. No. 3,791,376, Rybak, Feb. 12, 1974.
4. U.S. Pat. No. 3,123,066, Brumley, Mar. 3, 1964.
5. U.S. Pat. No. 3,136,310, Meltzer, June 9, 1964.
6. U.S. Pat. No. 3,498,286, Polanyi et al, Mar. 3, 1970.
7. U.S. Pat. No. 3,814,081, Mori, June 4, 1974.
8. U.S. Pat. No. 3,822,695, Takayama, July 9, 1974.
9. U.S. Pat. No. 3,847,483, Shaw et al, Nov. 12, 1974.
10. U.S. Pat. No. 3,983,864, Sielaff et al, Oct. 5, 1976.
11. U.S. Pat. No. 3,952,730, Key, Apr. 27, 1976.

What is claimed is:

1. A catheter for use in making at least one blood-related measurement including the partial pressure of at least one blood gas comprising:
    wall means defining chamber means for light absorption spectral analysis of said one blood gas, said chamber means being of a size small enough to allow the chamber to be placed within a blood carrying member of a human body, said chamber means having first and second spaced apart regions defining a void space therebetween;
    said wall means including a semi-permeable membrane at said first region of the chamber means, said wall means having an interior surface facing toward said chamber means, said semi-permeable membrane being permeable to at least said one blood gas and substantially not permeable to blood whereby when the semi-permeable membrane is placed in contact with blood it allows said one blood gas to pass through the semi-permeable membrane into the chamber means to fill the void space and substantially prevents the blood from passing through the semi-permeable membrane into the chamber means so that the blood gas in the chamber means is separated from the blood;
    first elongated light-conducting means for conducting light to said second region of said chamber means so that the light can pass along a light path through said void space and through the blood gas in said chamber means and be at least partially absorbed by said one blood gas;
    second elongated light-conducting means for conducting light away from the chamber;
    means for attaching the first and second light-conducting means to said chamber means;
    a reflector within said chamber means including a reflective coating on said interior surface of said membrane for receiving light at said first region of the chamber means after the light has passed through at least some of the void space and the blood gas in the chamber means, the light path from the first elongated light-conducting means to the reflector being unobstructed except for the blood gas in the chamber means, said reflector reflecting at least some of the light it receives toward the second elongated light-conducting means for transmission away from the chamber means whereby an indication of the partial pressure of said one blood gas can be obtained; and
    said semi-permeable membrane being resiliently deformable into the void space by the blood with which it is placed in contact whereby blood pressure and heart rate information can be obtained.

2. A catheter as defined in claim 1 wherein said chamber is generally cylindrical and has a length greater than its diameter, said semi-permeable membrane being at one end of the cylindrical chamber and both of said elongated light-conducting means terminating at the other end of said cylindrical chamber.

3. A method of making at least one blood-related measurement including the partial pressure of at least one blood gas comprising:

providing a sensor which includes wall means defining a chamber with the wall means including a semi-permeable membrane which is permeable to at least said one blood gas and substantially not permeable to blood;

performing in vivo spectral analysis by light absorption through said at least one blood gas utilizing said sensor; and said step of performing including positioning the sensor with the semi-permeable membrane contacting blood and allowing at least said one blood gas to flow through the permeable wall into the chamber, directing light into the sensor and through the blood gas therein with the light having a wave length which is highly absorbed by said one blood gas, reflecting the light which has passed through at least some of the blood gas in the chamber out of the chamber, and comparing a characteristic of the light directed into the chamber with a characteristic of the light reflected out of the chamber to obtain an indication of the partial pressure of said one blood gas.

4. A method as defined in claim 3 wherein said step of providing includes providing the membrane as a resiliently deformable membrane and providing a reflective coating on the interior surface of the membrane, carrying out said step of reflecting utilizing said reflective coating, allowing the blood to resiliently deform the membrane to alter the reflectance from the reflective coating, and using the altered reflectance to obtain an indication of a blood pressure related measurement.

5. An apparatus for in vivo measurement of two blood gas partial pressures comprising:

wall means defining a chamber adapted to be inserted into the blood stream to be analyzed, said chamber having first and second spaced apart regions defining a void space therebetween, said wall means including a semi-permeable membrane at said first region which is permeable to at least said two blood gases and is substantially not permeable to blood whereby when the membrane is placed in contact with blood, it allows said two blood gases to pass through the membrane into the chamber and substantially prevents the blood from passing through the semi-permeable membrane into the chamber so that the two blood gases in the chamber are separated from the blood;

first and second light sources, said first source producing light of a wavelength suitable for absorption analysis of one of said two blood gases, said second source producing light of a wavelength suitable for the absorption analysis of a second of said blood gases;

first light-conducting means for conducting the light from said sources to said second region of the chamber so that the light can pass through the void space and the blood gases in said chamber and be at least partially absorbed thereby;

first means for alternately pulsing the light from said first and second sources through said first light-conducting means to said chamber;

second light-conducting means for conducting light away from the chamber;

means for attaching the first light-conducting means to said chamber;

a reflector in said chamber for receiving light from said first light-conducting means after the light has passed through at least some of the blood gases in the chamber, said reflector reflecting at least some of the light it receives toward the second light-conducting means;

means for attaching the second light conducting means to said chamber at a position to receive light reflected by said reflector;

first and second light detectors;

means for alternately pulsing the light from said second light-conducting means to said first and second detectors whereby said first and second detectors receive at least some of the light from said first and second light sources, respectively, each of said detectors including means for providing an output signal responsive to a characteristic of the light received by such detector;

means responsive to the output signals from said first and second detectors to provide indications of the partial pressures of said first and second blood gases, respectively;

said semi-permeable membrane having an interior surface facing toward said chamber and said reflector includes a reflective coating on said interior surface; and said semi-permeable membrane being resiliently deformable into the void space by the blood with which it is placed in contact whereby blood pressure and heart rate information can be obtained.

6. An apparatus as defined in claim 5 wherein said apparatus includes means responsive to at least one of said output signals for providing an indication of at least one blood pressure related parameter.

7. An apparatus as defined in claim 5 wherein said first pulsing means includes a rotatably mounted wheel and at least two prisms mounted on said wheel for the reflection of light from said first source, said prisms being spaced apart to define spaces therebetween for the direct transmission of light from said second source to said first light-conducting means.

* * * * *

UNITED STATES PATENT OFFICE
CERTIFICATE OF CORRECTION

Patent No. 4,201,222          Dated May 6, 1980

Inventor(s) Thomas Haase

It is certified that error appears in the above-identified patent and that said Letters Patent are hereby corrected as shown below:

On the title page, insert "Assignee: Theodore S. Wentworth, Jr."

Signed and Sealed this

Tenth Day of March 1981

[SEAL]

Attest:

RENE D. TEGTMEYER

Attesting Officer      Acting Commissioner of Patents and Trademarks